United States Patent
Mannar et al.

(10) Patent No.: US 8,165,849 B2
(45) Date of Patent: Apr. 24, 2012

(54) MEDICAL EQUIPMENT MONITORING METHOD AND SYSTEM

(75) Inventors: Kamal Mannar, Pewaukee, WI (US); Douglas E. Starasinich, Crest Hill, IL (US)

(73) Assignee: General Electric Company, Niskayuna, NY (US)

( * ) Notice: Subject to any disclaimer, the term of this patent is extended or adjusted under 35 U.S.C. 154(b) by 216 days.

(21) Appl. No.: 12/172,495

(22) Filed: Jul. 14, 2008

(65) Prior Publication Data
US 2010/0011251 A1   Jan. 14, 2010

(51) Int. Cl.
*G06F 19/00* (2006.01)
(52) U.S. Cl. .......... 702/189; 702/104; 702/183
(58) Field of Classification Search .......... 702/45, 702/104, 105, 183, 189, 191, 195; 73/1.06, 73/861.22, 861.23
See application file for complete search history.

(56) References Cited

U.S. PATENT DOCUMENTS

| | | | |
|---|---|---|---|
| 5,439,483 A * | 8/1995 | Duong-Van | 607/5 |
| 5,668,850 A | 9/1997 | Abdel-Malek | |
| 5,995,910 A | 11/1999 | Discenzo | |
| 6,567,752 B2 | 5/2003 | Cusumano et al. | |
| 6,601,005 B1 * | 7/2003 | Eryurek et al. | 702/104 |
| 6,828,889 B1 | 12/2004 | Zaput | |
| 7,020,569 B2 | 3/2006 | Cao et al. | |
| 7,099,852 B2 * | 8/2006 | Unsworth et al. | 706/23 |
| 7,103,509 B2 | 9/2006 | Shah et al. | |
| 2002/0128731 A1 | 9/2002 | Wegerich et al. | |
| 2005/0109049 A1 | 5/2005 | Chan | |

OTHER PUBLICATIONS

Xiaoli et al., On-Line tool condition monitoring system with wavelet fuzzy nearual network', 1997, Journal of Intelligent Manufacturing, pp. 271-276.*
Li et al., 'Real-Time Tool Condition Monitoring Using Wavelet Transforms and Fuzzy Techniques', Aug. 2000, IEEE Publication, vol. 30, No. 3, pp. 352-357.*

* cited by examiner

*Primary Examiner* — Mohamed Charioui
*Assistant Examiner* — Elias Desta
(74) *Attorney, Agent, or Firm* — Fletcher Yoder, P.C.

(57) ABSTRACT

A system and method to facilitate device monitoring and servicing is provided. In one embodiment, a system may include a medical device having at least one component, and monitoring circuitry configured to measure operational data of the component. The system can also include a data processing system configured to analyze the operational data and to output a report based on such analysis. The analysis, in turn, may include applying a transform to the operational data and comparing one or more actual coefficient and threshold coefficient characteristics.

13 Claims, 9 Drawing Sheets

MEDICAL EQUIPMENT MONITORING METHOD AND SYSTEM

BACKGROUND

The present disclosure relates generally to the field of service delivery. More specifically, the present disclosure relates to a system and method to facilitate device monitoring and servicing.

In a variety of industrial, commercial, medical, and research contexts, various pieces of equipment may be employed on a day-to-day basis to accomplish or facilitate the work being performed at a facility. In many instances, the facility may rely upon a third party to provide service for some or all of the equipment at the site to ensure that the equipment remains operational and available. For example, in an industrial setting, production equipment or computer resources that are in operation in a continuous or near-continuous manner may be serviced by an off-site party that provides servicing as needed or requested. Similarly, hospitals, clinics, and research facilities may utilize another party to service some or all of the diagnostic, monitoring, and/or imaging equipment at a site so that the equipment remains available where and when it is needed. It is noted that failure of such resources or equipment may, in some cases, significantly inconvenience the owners and users of the failed systems.

BRIEF DESCRIPTION

There is a need for a system and method to monitor device operation and to manage service delivery in an efficient and cost-effective manner. There is also a need for a system and method to calculate when a device should be serviced, what service should be performed, and whether such service was effective. The subject matter described herein is operable to address the needs and concerns described above. Certain aspects commensurate in scope with the originally claimed invention are set forth below. It should be understood that these aspects are presented merely to provide the reader with a brief summary of certain forms various embodiments of the invention might take, and that these aspects are not intended to limit the scope of the invention. Indeed, the invention may encompass a variety of aspects that may not be set forth below.

In accordance with one embodiment of the subject matter described herein, a system includes a medical device having at least one component, and monitoring circuitry configured to measure operational data of the device component. The system may also include a data processing system configured to analyze the operational data of the device component and to output a report based at least in part on such analysis. The analysis of the operational data may include applying a transform, such as a wavelet transform, to the operational data to separate different signal components in the operational data. The analysis may also include predicting at least one of a failure rate or a survival rate of the device over a time period based at least in part on comparison of an actual coefficient characteristic of the transform to one or more expected coefficient characteristics.

According to another embodiment, a method includes receiving operational data of a device, the operational data including a feature of interest. Further, the method may include applying a transform to the operational data to extract the feature of interest from the operational data. Additionally, the method may include comparing a characteristic of a transform coefficient associated with the extracted feature of interest to a threshold derived from a population of similar devices. The method may also include outputting a report indicative of the operating state of the device based at least in part on the comparison.

According to yet another embodiment, a manufacture includes one or more computer-readable media having executable instructions stored thereon. The executable instructions may include instructions to apply a transform to operational data of a device to extract a feature of interest from the operational data. The executable instructions may further include instructions to compare a characteristic of a transform coefficient associated with the extracted feature of interest to a threshold derived from a population of similar devices, and instructions to output a report based at least in part on the comparison.

Various refinements of the features noted above may exist in relation to various aspects of the subject matter described herein. Further features may also be incorporated in these various aspects as well. These refinements and additional features may exist individually or in any combination. For instance, various features discussed below in relation to one or more of the illustrated embodiments may be incorporated into any of the above-described embodiments of the present invention alone or in any combination. Again, the brief summary presented above is intended only to familiarize the reader with certain aspects and contexts of the subject matter herein without limitation to the claimed subject matter.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

One or more specific embodiments of the presently disclosed subject matter will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Moreover, while the term "exemplary" may be used herein in connection to certain examples of aspects or embodiments of the presently disclosed subject matter, it will be appreciated that these examples are illustrative in nature and that the term "exemplary" is not used herein to denote any preference or requirement with respect to a disclosed aspect or embodiment. Further, any use of the terms "top," "bottom," "above," "below," other positional terms, and variations of these terms is made for convenience, but does not require any particular orientation of the described components.

Figure 1:
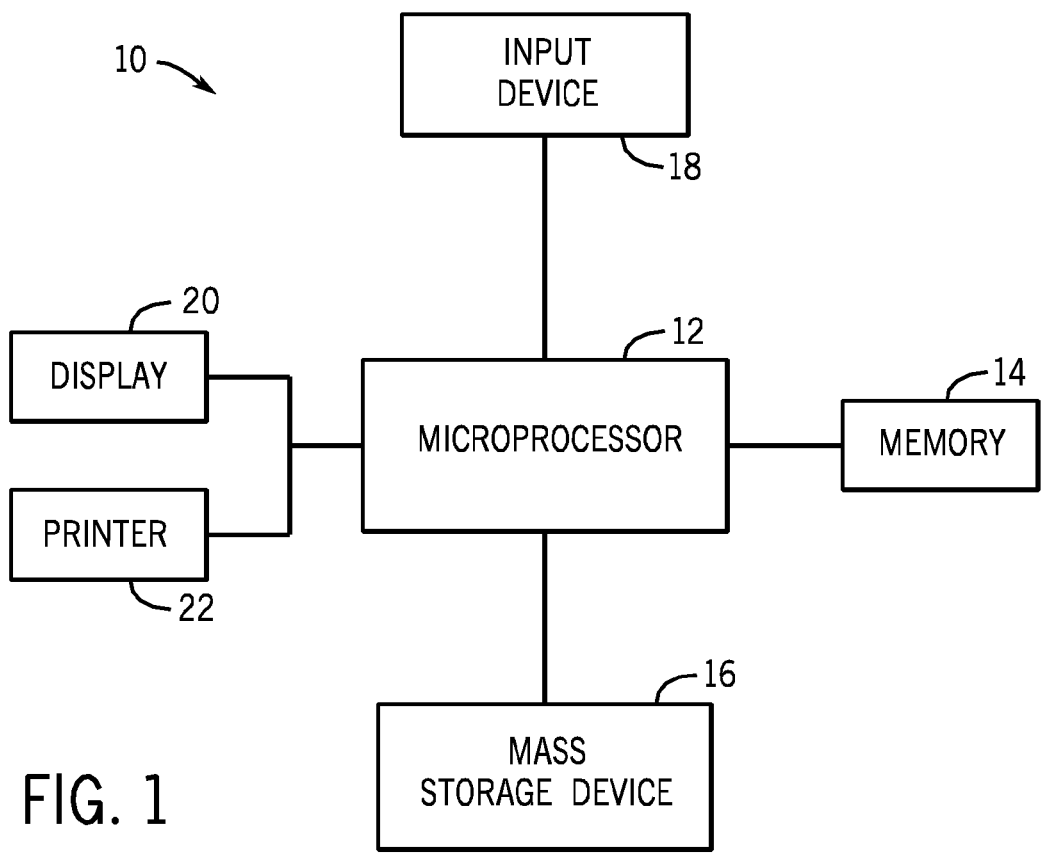
FIG. 1 is a block diagram of one embodiment of an exemplary processor-based device or system in accordance with the subject matter described herein.

Turning now to the drawings, and referring first to FIG. 1, an embodiment of a processor-based system 10 for use in conjunction with the present subject matter is depicted. The exemplary processor-based system 10 may be a general-purpose computer, such as a personal computer, configured to run a variety of software, including software implementing all or part of the functionality described herein. Alternatively, in other embodiments, the processor-based system 10 may comprise, among other things, a mainframe computer, a distributed computing system, or an application-specific computer or workstation configured to implement all or part of the presently described functionality based on specialized software and/or hardware provided as part of the system. Further, the processor-based system 10 may include either a single processor or a plurality of processors to facilitate implementation of the presently disclosed functionality.

In one embodiment, the exemplary processor-based system 10 includes a microcontroller or microprocessor 12, such as a central processing unit (CPU), which executes various routines and processing functions of the system 10. For example, the microprocessor 12 may execute various operating system instructions as well as software routines configured to effect certain processes and stored in or provided by a manufacture including one or more computer readable-media (at least collectively storing the software routines), such as a memory 14 (e.g., a random access memory (RAM) of a personal computer) or one or more mass storage devices 16 (e.g., an internal or external hard drive, a solid-state storage device, CD-ROM, DVD, or other storage device). In addition, the microprocessor 12 processes data provided as inputs for various routines or software programs, such as data provided as part of the present subject matter described herein in computer-based implementations.

Such data may be stored in, or provided by, the memory 14 or mass storage device 16. Alternatively, such data may be provided to the microprocessor 12 via one or more input devices 18. The input devices 18 may include manual input devices, such as a keyboard, a mouse, or the like. In addition, the input devices 18 may include a network device, such as a wired or wireless Ethernet card, a wireless network adapter, or any of various ports or devices configured to facilitate communication with other devices via any suitable communications network, such as a local area network or the Internet. Through such a network device, the system 10 may exchange data and communicate with other networked electronic systems, whether proximate to or remote from the system 10.

Results generated by the microprocessor 12, such as the results obtained by processing data in accordance with one or more stored routines, may be provided to an operator via one or more output devices, such as a display 20 and/or a printer 22. Based on the displayed or printed output, an operator may request additional or alternative processing or provide additional or alternative data, such as via the input device 18. Communication between the various components of the processor-based system 10 may typically be accomplished via a chipset and one or more busses or interconnects which electrically connect the components of the system 10. In one embodiment, the exemplary processor-based system 10 can be configured to facilitate monitoring and service delivery for one or more systems, such as medical systems, as discussed in greater detail below with respect to FIGS. 2-10.

The processor based-system 10 may be configured to facilitate analysis of operational data from functional systems and to also facilitate management of service delivery with respect to such systems. One or more embodiments of such functional systems may include a medical system (e.g., an imaging system, a diagnostic system, a monitoring system, or the like), although the presently disclosed subject matter may be broadly applicable to non-medical system embodiments as well. In one embodiment, the processor-based system 10 can be configured to extract one or more features from operational data of a system and configured to combine such features with one or more non-parametric reliability models for system failure prediction and system event impact analysis, as described in further detail below. Further, the processor-based system 10 may facilitate determination of an optimal service action from multiple potential service actions, calculation of an optimal time for performing the service action (e.g., based on a predicted time to failure), and analysis of the effectiveness of any performed service action.

Figure 2:
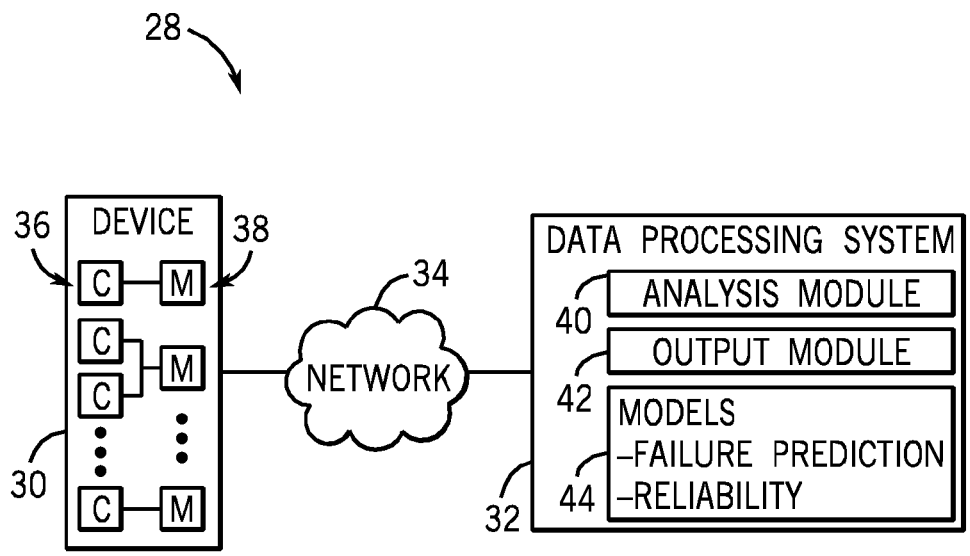
FIG. 2 depicts an embodiment of a networked system of medical devices and a data processing system in accordance with the subject matter described herein.

By way of example, a system 28 is depicted in FIG. 2 in accordance with one embodiment. In this presently illustrated embodiment, one or more devices 30 (e.g., medical devices) can be communicatively coupled to a data processing system 32 via a network 34. The data processing system 32 may include the processor-based system 10 illustrated in FIG. 1, although it is noted that, in other embodiments, the data processing system 32 may include various components or systems different than, or in addition to, those illustrated in FIG. 1. Additionally, the network 34 may include one or more of a local area network (LAN) or a wide area network (WAN) (e.g., the Internet), as well as various other components that facilitate communication, including switches, routers, servers or other computers, network adapters, communications cables, and so forth.

In one embodiment, the devices 30 may include medical imaging devices of one or more modalities, such as magnetic resonance (MR), computed tomography (CT), positron emission tomography (PET), X-ray, tomosynthesis, or the like. It should be appreciated, however, that the present teachings may also or instead be used in consort with patient monitors, diagnostic devices, other medical resources, or some combination of these devices and systems. Such other medical resources may include, but are not limited to, data storage or processing systems (e.g., computer workstations or servers), picture archiving and communication systems (PACS), radiological information systems (RIS), and so forth. Indeed, as noted above, while the presently illustrated embodiment may be described with reference to a plurality of medical devices, other embodiments of system 28 may include non-medical devices alone, or include both medical devices and non-medical devices.

A device 30 may include one or more functional components 36 that operate in a manner that contributes to device functionality. In medical devices, such components 36 may include an X-ray tube, a magnetic coil, a power supply, components of a heating system, components of a refrigeration system (e.g., a coldhead, as discussed in greater detail below), and so forth. The device 30 can also include various monitoring circuitry 38 configured to collect operational data of the device 30 and the components 36, such as by way of sensors configured to collect such data. While the monitoring circuitry 38 of the presently illustrated embodiment may be integrated with the device 30, it is noted that, in other embodiments, the monitoring circuitry 38 (and any associated sensors) may be separate from the device 30.

In turn, the data processing system 32 may include a number of hardware and/or software modules to process the operational data collected by the monitoring circuitry 38. For example, in one embodiment, the data processing system 32 may include an analysis module 40 and an output module 42. In this embodiment, the analysis module 40 may be configured to apply one or more mathematical models 44 (e.g., failure prediction models, reliability models, event-effect analysis models, and the like, which may, in at least some embodiments, be non-parametric models) to the operational data, and the results of such processing may be output via the output module 42.

The data processing system 32 may be configured to perform one or more steps of various exemplary methods for monitoring and servicing devices, including, but not limited to, those methods discussed in greater detail below. Any or all of the steps performed by the data processing system 32 may be performed as part of a software-based and/or spreadsheet-based application having stored routines adapted to effect the steps described below. In other embodiments, however, the steps performed by the system 32 may be performed via application-specific hardware or circuitry configured to perform such steps. Additionally, it will be appreciated that the various exemplary steps of the presently disclosed methods may be performed in any suitable order, and need not be performed in the order described below.

Figure 3:
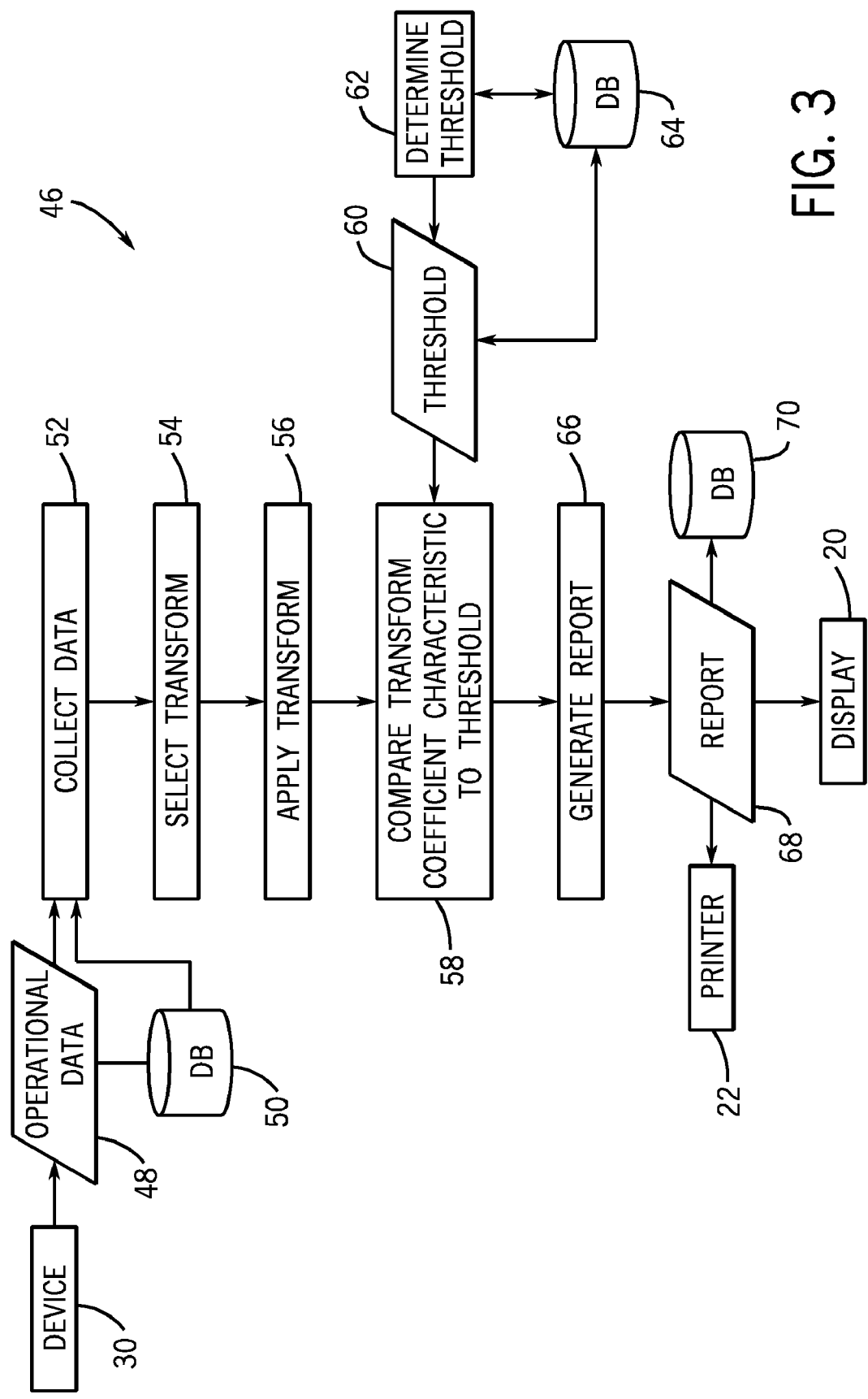
FIG. 3 is a flow diagram of an embodiment of a device monitoring method in accordance with the subject matter described herein.

For example, an exemplary device monitoring method 46 is illustrated in FIG. 3 in accordance with one embodiment. In a step 52 of the method 46, operational data 48 for device 30 may be obtained directly from the device 30 or from some other data source, such as a database 50. In other embodiments, additional, non-operational data may also or instead be collected in this step.

Further, one or more mathematical transforms may be selected from a group of such transforms and applied to the collected data in steps 54 and 56, respectively. For instance, a selected mathematical transform may be applied to the operational data 48 to extract one or more features of interest, such as, but not limited to, specific frequency sub-bands from the data. In some embodiments, such feature extraction may facilitate event detection and failure prediction for the monitored systems and components (e.g., device 30 and components 36). Any of various suitable transforms may be applied to extract desired features from the operational data 48. For instance, in one embodiment, the step 56 includes applying a discrete wavelet transform (DWT). In other embodiments, however, the applied transform may include a different wavelet transform, a principal component analysis (PCA) transform, a Fourier transform (e.g., a fast Fourier transform (FFT)), and so forth.

The method 46 may also include comparing one or more transform coefficients (or data derived from such coefficients), in a step 58, to a threshold 60. In one embodiment, the threshold 60 is determined in a step 62 through use of a failure prediction model and training data to provide a point of reference based on other systems or components similar to the analyzed device 30 or component 36. The determined threshold 60 may also be stored in a database 64 for future access. In one embodiment, a discrete wavelet transform can be applied to the operational data 48 to generate approximate and detail coefficients, and the variance of one or more of these coefficients (representative of operation of the device 30) is compared to a threshold 60 indicative of expected operation (which may be based on normal operation, minimum or maximum performance expectations, or the like) to determine whether operation of the device 30 is an outlier with respect to expected operational parameters. The comparison of step 58 may also, or instead, include other comparative processes. In another embodiment, for instance, a failure probability (e.g., probability that the device 30 (or component 36 thereof) will fail within a given time period, such as twenty days) may be calculated for the device 30 from the operational data 48 and compared to a threshold failure probability, to facilitate servicing of the device 30 when failure probability exceeds the threshold failure probability. In one embodiment, a failure probability model may include a proportional hazards prediction model, such as that described in greater detail below, to facilitate calculation of the failure probabilities.

In a step 66, a report 68 may be generated based on the comparison performed in the step 58. For example, the report 68 may include an indication of imminent component or device failure, and may suggest servicing of the component 36 or device 30. The report 68 may be output in a variety of manners. For instance, the report 68 may be output to, and stored in, a database 70 to facilitate future access or processing, or may be output in a human-readable form, such as via the display 20 and printer 22.

Figure 4:
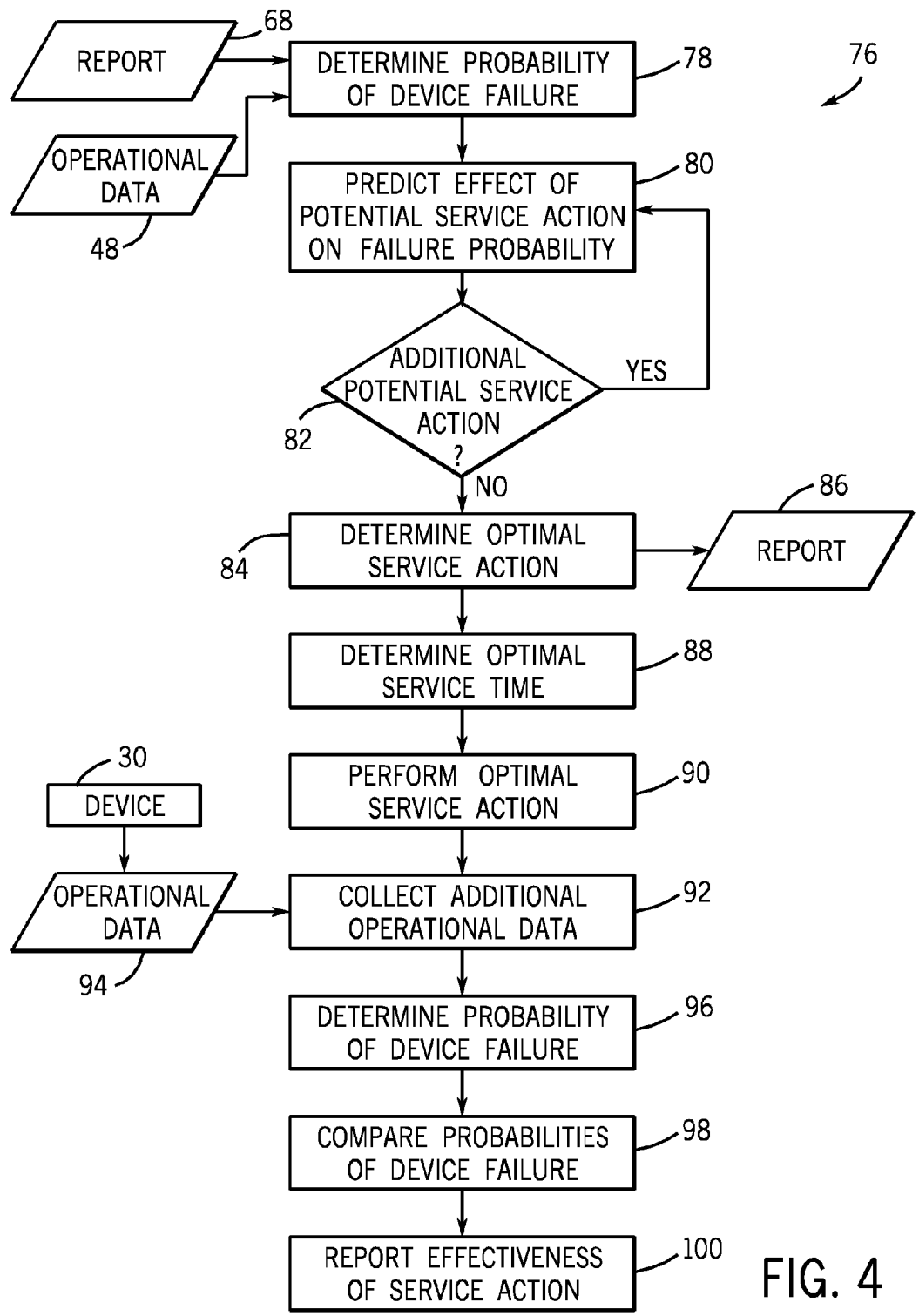
FIG. 4 is a flow diagram of an embodiment of a service delivery method in accordance with the subject matter described herein.

An exemplary method for determining an optimal service action, and for measuring the impact of performance of the optimal service action, is generally depicted in FIG. 4 in accordance with one embodiment. The exemplary method 76 may include determining a probability of device or component failure in a step 78. In one embodiment, a feature-based failure prediction model may be applied to various data, such as the operational data 48 (e.g., wavelet features or other features extracted therefrom), data contained within the report 68, or the like, to facilitate determination of the probability of failure of a particular device 30 or component 36. It is noted that such a failure prediction model may, in one embodiment, generally detect both data trends and deterioration of the monitored device 30 or component 36. Additionally, the failure prediction model may also be used to detect device events that impact the life expectancy or failure probability of the monitored device 30 or component 36.

Step 80 of the method 76 may include predicting the effect of one or more potential service actions with respect to the device 30 (or component 36) on the probability of failure of that device (or component). The aforementioned prediction may, in some embodiments, be generated via a non-parametric reliability model that integrates an extracted feature, as discussed above. Again, such a non-parametric reliability model may include a proportional hazards model that uses wavelet coefficients derived from the operational data 48 to determine the probability of failure of the device within a given time period. Further, as generally indicated by block 82, the method 76 may iteratively predict the effect of each service action of a number of potential service actions (e.g., various repair and/or replacement options) on the failure probability for the monitored component 36 or device 30. Based at least on these calculated failure probabilities, an optimal service action may be determined in a step 84. Using the models described above, or some other mathematical models, an estimated time to failure may be calculated for the device 30, or a component 36 thereof, and an optimal time for servicing (e.g., a point in time before expected failure of the device 30 or component 36) may be calculated in a step 88. Additionally, one or both of the optimal service action and the optimal service time may be output, such as via a report 86.

In one embodiment, the method 76 may also include performing a service action (e.g., the determined optimal service action) in a step 90. Further, in a step 92, additional operational data 94 may be collected from the device 30 following such servicing. The operational data 94 collected after performance of the optimal service action may be analyzed, in a step 96, to determine an updated failure probability for the serviced device 30 or component 36. It is noted that this updated failure probability may be calculated in an identical or similar manner to that described above with respect to the determination of a failure probability based on operational data 48 collected prior to performance of the optimal service action. In other embodiments, however, one or both of steps 78 and 96 for determining failure probabilities may be performed in some other suitable manner.

Additionally, the device failure probabilities determined before and after, respectively, performance of the optimal service action may be compared in a step 98, and the effectiveness of the performance of the optimal service action may be reported in a step 100. For instance, a decrease in the device failure probability following performance of the optimal service action (in comparison to the device failure probability determined prior to the performance of the optimal service action) may indicate the optimal service action had a positive impact on the reliability of the serviced device. Alternatively, an unchanged or higher device failure probability after performance of the optimal service action may generally indicate that the optimal service action was not effective. Such ineffectiveness may, in some cases, suggest that the service action was improperly performed or that a replacement part was defective.

While the presently illustrated embodiment is described above as including a step 98 of comparing device failure probabilities it is noted that the effectiveness of the optimal service action may be determined through other comparison processes and criteria in other embodiments. For instance, in one embodiment, the impact of the optimal service action predicted in step 80 (which may include, but is not limited to, a predicted change in device failure probability attributable to performance of the optimal service action) may be compared to the actual impact of the optimal service action (e.g., actual change in device failure probability resulting from performance of the optimal service action). Such a comparison may be used to ensure that a service action performed on a device 30 or component 36 is properly performed and restores operation of the device 30 or component 36 to an expected level or range.

Figure 5:
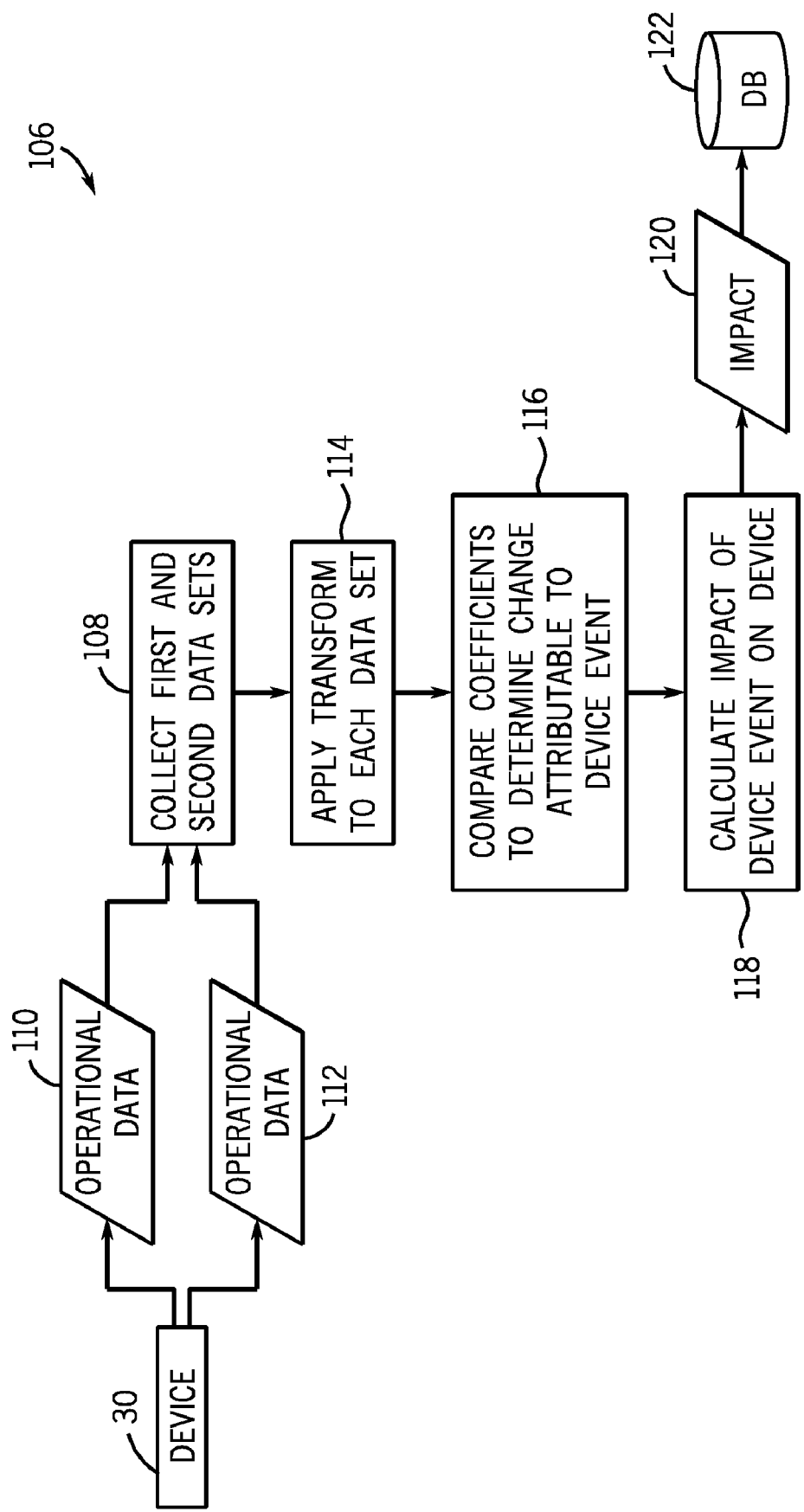
FIG. 5 is a flow diagram of an exemplary device monitoring method in accordance with one aspect of the presently described subject matter.

Further, an exemplary method 106 for measuring the impact of an event, such as a service event or a transient event, on a failure probability, a survival probability, an expected time to failure, or the like, for the device 30 or component 36 is illustrated in FIG. 5 in accordance with one embodiment. The method 106 may include a step 108 of collecting a first set of operational data 110 prior to occurrence of the event of interest, and a second set of operational data 112 collected following the occurrence of the event of interest. In a step 114, a transform may be applied to each data set of the operational data sets 110 and 112. In one embodiment, the applied transform may be a wavelet transform, such as a discrete wavelet transform, although other transforms may be employed, as generally described above. The method 106 may also include a step 116 of comparing coefficients of each set of the transformed data to one another to determine a change in the data attributable to the event of interest, and an impact 120 of the device event on various device characteristics, such as life expectancy, failure probability, survival rate, or the like, may be calculated in a step 118. Further, the calculated impact 120 may be output to, and stored in, a database 122 for future reference, or may be output to a user.

As noted above, the data processing system 32 may facilitate monitoring and analysis of a variety of devices 30, including medical devices. By way of example, several exemplary medical devices and components, along with exemplary implementations of certain aspects of the present subject matter, are discussed below in accordance with various embodiments illustrated in FIGS. 6-9. It is noted, however, that these embodiments are provided merely as examples of possible features of the present subject matter, and that other embodiments may include other features in addition to, or in place of, those discussed herein.

Figure 6:
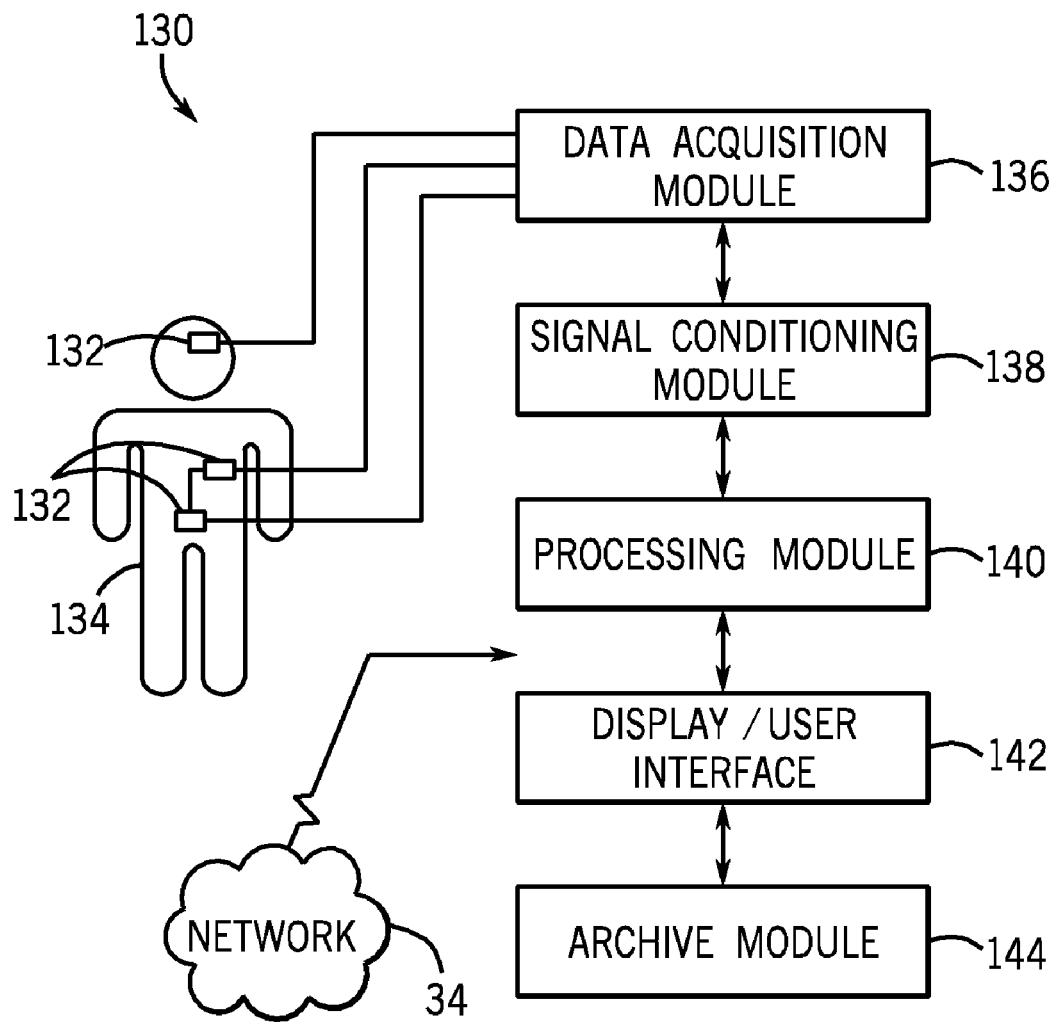
FIG. 6 is a general diagrammatical representation of an exemplary data acquisition resource, including various general components or modules for acquiring electrical data representative of body function and state, which may be monitored and serviced in accordance with one embodiment of the subject matter described herein.

In some embodiments, an exemplary medical device 30 may include a data acquisition system 130 having certain typical modules or components as indicated generally in FIG. 6. These components may include sensors or transducers 132, which may be placed on or about a patient 134 to detect certain parameters of interest that may be indicative of medical events or conditions. Thus, the sensors 132 may detect electrical signals emanating from the body or portions of the body, pressure created by certain types of movement (e.g. pulse or respiration), or parameters such as movement, reactions to stimuli, and so forth. The sensors 132 may be placed on external regions of the body, but may also include placement within the body, such as through catheters, injected or ingested means, capsules equipped with transmitters, and so forth.

The sensors generate signals or data representative of the sensed parameters. Such raw data may be transmitted to a data acquisition module 136. The data acquisition module may acquire sampled or analog data, and may perform various initial operations on the data, such as filtering, multiplexing, and so forth. The data may then be transmitted to a signal conditioning module 138 where further processing is performed, such as for additional filtering, analog-to-digital conversion, and so forth. A processing module 140 then receives the data and performs processing functions, which may include simple or detailed analysis of the data. A display/user interface 142 permits the data to be manipulated, viewed, and output in a user-desired format, such as in traces on screen displays, hardcopy, and so forth. The processing module 140 may also mark or analyze the data for marking such that annotations, delimiting or labeling axes or arrows, and other indicia may appear on the output produced via interface 142. Finally, an archive module 144 serves to store the data either locally within the resource, or remotely. The archive module may also permit reformatting or reconstruction of the data, compression of the data, decompression of the data, and so forth. The particular configuration of the various modules and components illustrated in FIG. 6 will, of course, vary depending upon the nature of the resource and, if an imaging system, the modality involved. Finally, as represented generally at reference numeral 34, the modules and components illustrated in FIG. 6 may be directly or indirectly linked to external systems and resources via a network, which may facilitate transmission of data from the data acquisition system 130 to other devices or systems.

Data acquisition systems 130 may include a number of non-imaging systems capable of collecting desired data from a patient. For instance, the data acquisition systems 130 may include, among others, an electroencephalography (EEG) system, an electrocardiography (ECG or EKG) system, an electromyography (EMG) system, an electrical impedance tomography (EIT) system, an electronystagmography (ENG) system, a system adapted to collect nerve conduction data, or some combination of these systems. The data acquisition systems may also or instead include various imaging resources, as discussed below with respect to FIGS. 7 and 8.

Figure 7:
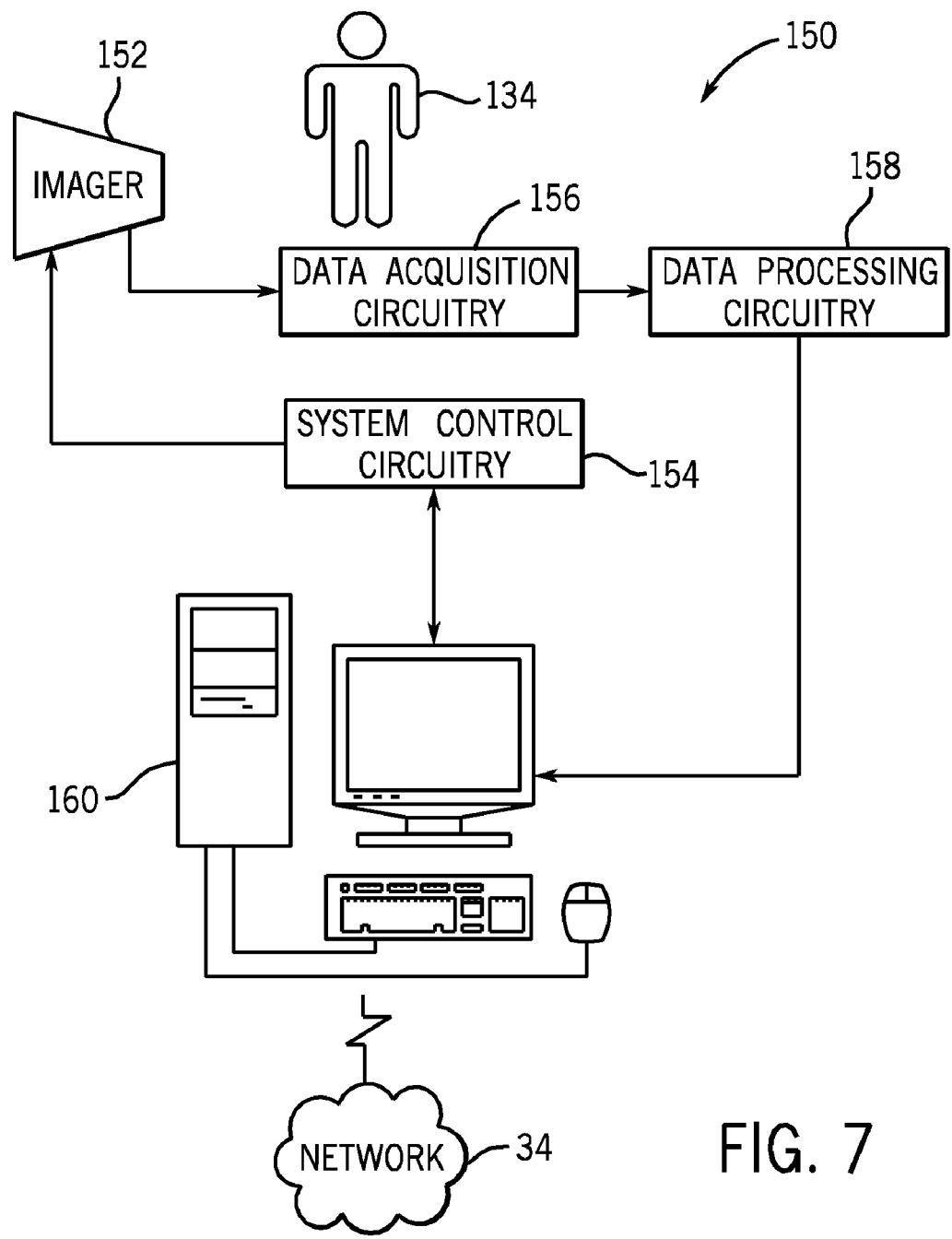
FIG. 7 is a general diagrammatical representation of certain functional components of a medical diagnostic imaging system that may be part of a data acquisition resource in accordance with one embodiment of the presently described subject matter.

Such imaging resources may be employed to diagnose medical events and conditions in both soft and hard tissue, and for analyzing structures and function of specific anatomies. Moreover, imaging systems are available which can be used during surgical interventions, such as to assist in guiding surgical components through areas which are difficult to access or impossible to visualize. FIG. 7 provides a general overview for exemplary imaging systems, while FIG. 8 offers somewhat greater detail into the major system components of a magnetic resonance (MR) imaging system.

Referring to FIG. 7, an imaging system 150 generally includes some type of imager 152 which detects signals and converts the signals to useful data. The imager 152 may operate in accordance with various physical principles for creating the image data, depending on the imaging modality. In general, however, image data indicative of regions of interest in a patient 134 are created by the imager either in a conventional support, such as photographic film, or in a digital medium.

The imager 152 may operate under the control of system control circuitry 154. The system control circuitry 154 may include a wide range of circuits, such as radiation source control circuits, timing circuits, circuits for coordinating data acquisition in conjunction with patient or table of movements, circuits for controlling the position of radiation or other sources and of detectors, and so forth. The imager 152, following acquisition of the image data or signals, may process the signals, such as for conversion to digital values, and forwards the image data to data acquisition circuitry 156. In the case of analog media, such as photographic film, the imaging system 150 may generally include supports for the film, as well as equipment for developing the film and producing hard copies that may be subsequently digitized. For digital systems, the data acquisition circuitry 156 may perform a wide range of initial processing functions, such as adjustment of digital dynamic ranges, smoothing or sharpening of data, as well as compiling of data streams and files, where desired. The data is then transferred to data processing circuitry 158 where additional processing and analysis are performed. For conventional media such as photographic film, the data processing system may apply textual information to films, as well as attach certain notes or patient-identifying information. For the various digital imaging systems available, the data processing circuitry perform substantial analyses of data, ordering of data, sharpening, smoothing, feature recognition, and so forth.

Ultimately, the image data is forwarded to some type of operator interface 160 for viewing and analysis. While operations may be performed on the image data prior to viewing, the operator interface 160 is at some point useful for viewing reconstructed images based upon the image data collected. It should be noted that in the case of photographic film, images are typically posted on light boxes or similar displays to permit radiologists and attending physicians to more easily read and annotate image sequences. The images may also be stored in short or long term storage devices, for the present purposes generally considered as included within the interface 160, such as picture archiving communication systems. The image data can also be transferred to remote locations via the network 34. It should also be noted that, from a general standpoint, the operator interface 160 affords control of the imaging system, typically through interface with the system control circuitry 154. Moreover, it should also be noted that more than a single operator interface 160 may be provided. Accordingly, the operator interface 160 may include an interface at an imaging scanner or station to regulate parameters involved in the image data acquisition procedure, and further include a different interface to manipulate, enhance, and view resulting reconstructed images.

Figure 8:
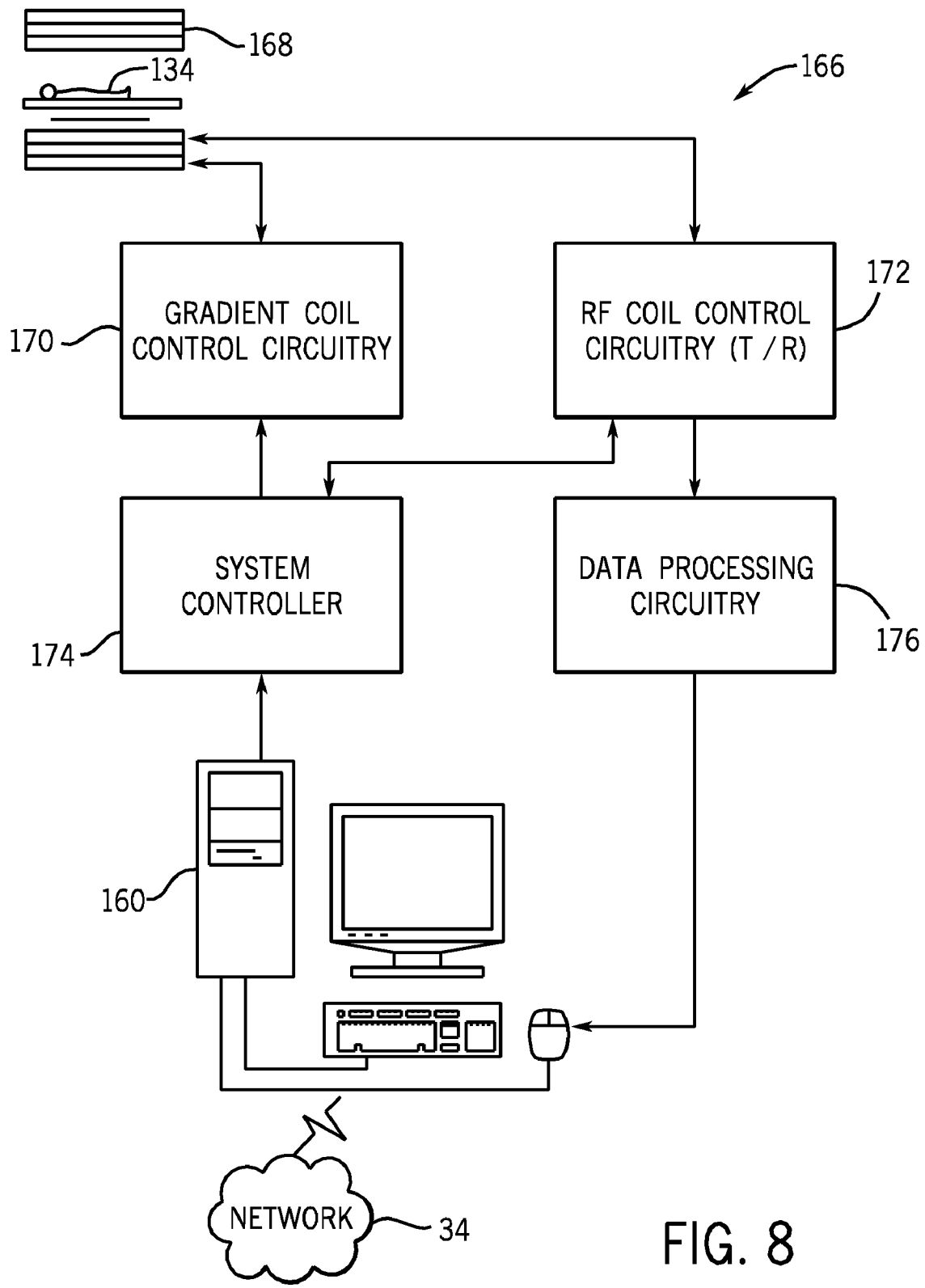
FIG. 8 is a diagrammatical representation of an exemplary magnetic resonance imaging system which may be employed in accordance with one embodiment of the subject matter described herein.

Turning to a more detailed example of the imaging system 150 that may be monitored and/or serviced in accordance with various exemplary processes described herein, a general diagrammatical representation of a magnetic resonance imaging system 166 is illustrated in FIG. 8. The system 166 includes a scanner 168 in which a patient 134 is positioned for acquisition of image data. The scanner 168 generally includes a primary magnet, such as magnet 171 (FIG. 9), for generating a magnetic field which influences gyromagnetic materials within the body of the patient 134. As the gyromagnetic materials, typically water and metabolites, attempt to align with the magnetic field, gradient coils produce additional magnetic fields which are orthogonally oriented with respect to one another. The gradient fields effectively select a slice of tissue through the patient for imaging, and encode the gyromagnetic materials within the slice in accordance with phase and frequency of their rotation. A radio-frequency (RF) coil in the scanner generates high frequency pulses to excite the gyromagnetic material and, as the material attempts to realign itself with the magnetic fields, magnetic resonance signals are emitted which are collected by the radio-frequency coil.

The scanner 168 is coupled to gradient coil control circuitry 170 and to RF coil control circuitry 172. The gradient coil control circuitry 170 permits regulation of various pulse sequences which define imaging or examination methodologies used to generate the image data. Pulse sequence descriptions implemented via the gradient coil control circuitry 170 are designed to image specific slices, anatomies, as well as to permit specific imaging of moving tissue, such as blood, and defusing materials. The pulse sequences may allow for imaging of multiple slices sequentially, such as for analysis of various organs or features, as well as for three-dimensional image reconstruction. The RF coil control circuitry 172 permits application of pulses to the RF excitation coil, and serves to receive and partially process the resulting detected MR signals. It should also be noted that a range of RF coil structures may be employed for specific anatomies and purposes. In addition, a single RF coil may be used for transmission of the RF pulses, with a different coil serving to receive the resulting signals.

The gradient and RF coil control circuitry 170 and 172 function under the direction of a system controller 174. The system controller 174 implements pulse sequence descriptions that define the image data acquisition process. The system controller 174 will generally permit some amount of adaptation or configuration of the examination sequence by means of an operator interface 160.

Data processing circuitry 176 receives the detected MR signals and processes the signals to obtain data for reconstruction. In general, the data processing circuitry 176 digitizes the received signals, and performs a two-dimensional fast Fourier transform on the signals to decode specific locations in the selected slice from which the MR signals originated. The resulting information provides an indication of the intensity of MR signals originating at various locations or volume elements (voxels) in the slice. Each voxel may then be converted to a pixel intensity in image data for reconstruction. The data processing circuitry 176 may perform a wide range of other functions, such as for image enhancement, dynamic range adjustment, intensity adjustments, smoothing, sharpening, and so forth. The resulting processed image data is typically forwarded to an operator interface for viewing, as well as to short or long-term storage, or may be forwarded to a data processing system for additional processing. As in the case of foregoing imaging systems, MR image data may be viewed locally at a scanner location, or may be transmitted to remote locations both within an institution and remote from an institution such as via the network 34.

Figure 9:
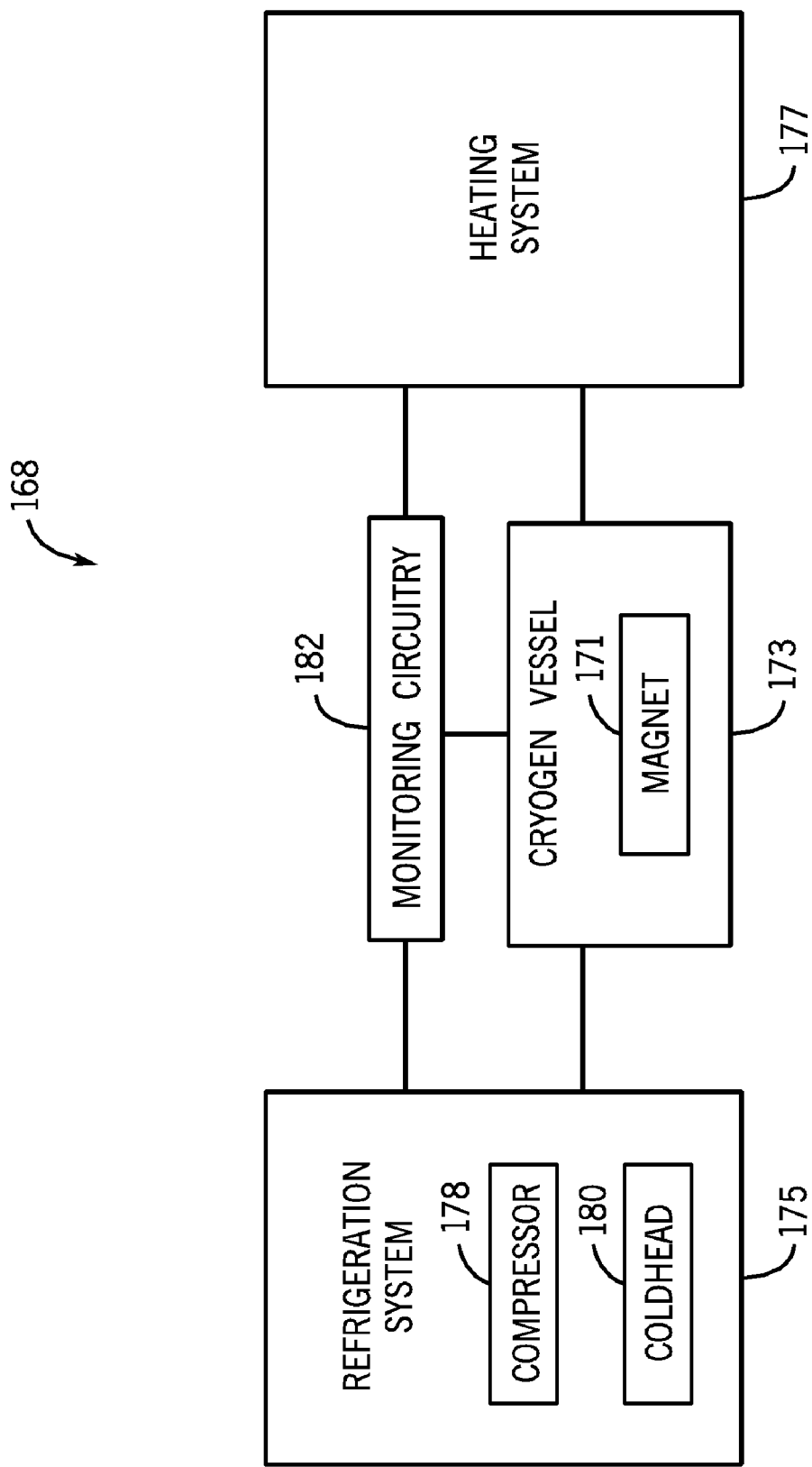
FIG. 9 is a block diagram generally representative of certain components and systems of an exemplary magnetic resonance imaging system in accordance with one embodiment of the subject matter described herein.

By way of further example, exemplary components of the scanner 168 are generally depicted in FIG. 9 in accordance with one embodiment. These exemplary components are provided merely for purposes of explanation, and it is noted that an actual scanner may include other components different from, or in addition to, those presently illustrated. The scanner 168 may include a magnet 171 such as a superconducting electromagnet. In one embodiment, the magnet 171 may include loops of coiled wire that generate a magnetic field as electricity travels through such loops. Additionally, such magnets are often disposed in a cryogen bath, such as within a cryogen vessel or cryostat 173, to maintain a low temperature and reduce the resistivity of the coiled wire, allowing greater magnetic field strengths and control. Often, the magnet 171 is cooled via liquid helium, although other cryogens could also be used.

To maintain the magnet 171 within a desired temperature range (and the cryostat 173 within a desired pressure range), the scanner 168 may also include a refrigeration system 175 and a heating system 177. In one embodiment, the refrigeration system 175 may include a compressor 178 and a coldhead 180, which work in combination to compress cryogen that evaporates due to ambient heat, and to cool and recondense the gas into a liquid state. The heating system 177 may include a number of further components, such as a resistive heating element, configured to increase temperature and pressure within the cryogen vessel 173. Additionally, the scanner 168 may include monitoring circuitry 182 to monitor various parameters of the scanner 168, including temperature within any of the components of the scanner 168, pressure within the cryogen vessel 173, the amount of cryogen within the cryogen vessel 173, the duty cycle of the heating system 177, and the like.

Again, the presently disclosed monitoring and analytical processes may be used with any of a wide array of systems or components to facilitate servicing thereof. By way of further example, a representative implementation of certain aspects of such processes in conjunction with the coldhead 180 is described below in accordance with one embodiment. It is noted, however, that the present subject matter is not limited to use with coldheads or to the particular implementation details of this representative example.

In one embodiment, the data processing system 32 may detect deterioration of a component 36, such as the coldhead 180, prior to change in a mean value of the parameters and may facilitate separation of transient events from actual component failures. Further, in one embodiment, the data processing system 32 may analyze the ability (or inability) of the coldhead 180 to maintain the pressure of cryogen vessel 173 within a desired range. Typically, pressure within the cryogen vessel 173 is controlled in a closed-loop manner, in which the heating system 177 operates to increase the cryogen vessel pressure and the coldhead 180 operates to decrease the cryogen vessel pressure. As a result, the pressure within the cryogen vessel 173 is generally cyclical within a desired operating range, but the cyclical nature of the data signal changes over time as various heating and cooling components age or otherwise degrade.

In one embodiment, the data processing system 32 may be operated to detect such changes in a data signal indicative of cryogen vessel pressure over time that indicate deterioration of the coldhead 180. It is noted that while a data signal representative of the pressure within the cryogen vessel 173 over a given time period may include a large cyclical component, as generally discussed above, the data signal may also include smaller, non-stationary characteristics (e.g., trends or sudden changes) and transitory characteristics that may correspond to deterioration of the coldhead 180. The non-stationary characteristics and the transitory characteristics may be separated from the cyclical component to facilitate coldhead failure prediction, as well as transient event detection and impact analysis.

For example, in one embodiment, changes in specific frequency sub-bands in the pressure data may provide an early indication (e.g., several days or weeks before failure) of coldhead deterioration, and a rising trend in vessel pressure may indicate imminent failure. Such indications may allow time to determine and perform a desired service action (e.g., cryogen recharge, coldhead replacement, or the like) before actual failure. In another embodiment, extracted data signal features may also be used to detect transitory events (e.g., resetting or shutoff of the compressor 178) that may affect the operational life of the coldhead 180, to classify these transitory events, to distinguish such transitory events from trends in the measured parameters of the coldhead 180, and to gauge (e.g., through event detection and modeling) the impact of such transient events on the life of coldhead 180.

As may be appreciated, a normal coldhead 180 and a deteriorated (but still functioning) coldhead 180 may both be capable of maintaining a mean cryogen vessel pressure within a desired range (e.g., from approximately 27 kPa to approximately 28 kPa). Consequently, typical failure models focusing only on the measured mean pressures of the respective normal and degraded coldheads 180 may not be capable of detecting differences between the deteriorated coldhead 180 and the normal coldhead 180 until the beginning of coldhead failure (e.g., when the mean pressure exceeds the maximum desired range). In one embodiment of the presently disclosed subject matter, however, the data processing system 32 may detect differences in the frequency and nature of the cyclical data, and may use such differences to provide earlier detection of coldhead deterioration and an extended prediction horizon in comparison to previous failure models.

In one embodiment, the data processing system 32 may employ a wavelet-based approach to model the cyclical nature of the signal and to detect trends and discontinuities in the signal. It is noted that wavelets are localized basis functions that are translated and dilated versions of a fixed mother wavelet function that provide time-frequency resolution for analyzing non-stationary and transient signals, and may be used to extract smaller informative components in a larger, repetitive signal. In the following non-limiting example, provided for the sake of explanation, wavelet decomposition may be used to decompose a data signal and to extract features of interest.

In one embodiment, the vessel pressure measurement obtained from a single system may be represented by:

$$y=(y(t_1), \ldots, y(t_N))'$$

obtained at equally spaced discrete time points $t=t_i$. The observed data may be assumed to be a realization of $y(t)=f(t)+\epsilon_t$, where $\epsilon_t$ is independent and identically distributed noise. The discrete wavelet transform (DWT) of y may be defined by $d=Wy$, where W is a N×N orthonormal wavelet transform matrix of the form:

$$W = \begin{bmatrix} h_{11} & h_{12} & \ldots & h_{1N} \\ h_{21} & h_{22} & \ldots & h_{2N} \\ \ldots & \ldots & \ldots & \ldots \\ h_{N1} & h_{N2} & \ldots & h_{NN} \end{bmatrix},$$

$d=(c_I, d_I, d_{I+1}, \ldots, d_J)'$, where $c_I, d_I, \ldots, d_J$ are wavelet coefficients at various scales. Further, $c_I$ may represent low frequency oscillations (approximation) while $d_J$ may represent the high frequency oscillations (details). It is noted that other transforms may be used instead of DWT, such as PCA or FFT, as noted above.

It is also noted that various optimal wavelet functions and decomposition levels may be selected for specific applications. In one embodiment, during normal operation of the coldhead 180, regular sharp transitions of vessel pressure between approximately 27 kPa and 28 kPa may occur due to the closed-loop nature of the system. These sharp transitions may generally result in larger values in specific detail wavelet coefficients (based on the affected frequency sub-band). As the coldhead 180 deteriorates, the transitions may change due to the inability of the coldhead to bring the vessel pressure down in a short duration of time and the number of cycles over a given period of time may reduce, resulting in a change in the selected wavelet coefficient values. The change in the selected wavelet coefficient values may be analyzed to detect and measure deterioration of the coldhead 180. In one embodiment, the selection of an appropriate wavelet coefficient may be based on maximizing the detection of transitions of coldhead cycle (i.e., the detail wavelet coefficient which maximizes this difference). Higher differentiability of the wavelet function allows greater differences in coefficient values between sharp and smooth transitions, providing better resolution of such transitions. Increased differentiability, however, may lead to larger support size for the wavelet and may reduce the ability to detect singularities.

Also, transient events in the life of a coldhead 180 may correspond to singularities (such as a large variation over a relatively short number of samples) caused by other cryogen cooling components (such as compressor failure or reset). In some instances, these events may cause a large increase in vessel pressure for a short duration of time. In one embodiment, these transient events may be better detected, and separated from actual failures, through use of a wavelet having a smaller support size. Still further, in one embodiment, trends in the measured pressure data for the coldhead 180 may be detected to predict coldhead failure. It is noted that long-term evolution of data, such as trends, corresponds to a low frequency component of the signal, which may be modeled by an approximation measuring slowly changing, coarse features of low frequency.

As such, in one embodiment, the selection of an optimum wavelet may be based on the differentiability and support size of the individual criteria of the deterioration, transient events and trend detection. Also, the decomposition level may be related to the frequency of the coldhead cycle, which may suggest use of a corresponding detail wavelet coefficient. In one embodiment, a Coif3 wavelet function with 'level 5' decomposition may be used by the data processing system 32 to provide the presently disclosed functionality.

Based on selected approximate and detail coefficients, a failure prediction model may be developed using training data to determine thresholds for wavelet features for deterioration and/or failure identification. In one embodiment, coldhead deterioration may be identified through comparison of the variance of the selected detail coefficient to a determined threshold to identify if the coldhead 180 of interest is an outlier compared to coldheads of similar age. Using a proportional hazards prediction model described below, the probability of failure in a given time period, such as twenty days, may be determined using the wavelet features. When the probability of failure increases to pre-determined threshold, the data processing system 32 may determine that the coldhead 180 is going to fail, and a service action (such as the optimal service action determined above) may be performed.

Additionally, one or more extracted features of a data signal, such as that described above, may be used in a non-parametric reliability model to model the impact of events on a monitored system or component. In one embodiment, use of such a model facilitates the combination of baseline deterioration of a system or component (e.g., coldhead 180) with respect to age, with the effect of individual events occurring in the system. Such a combination may generally allow the data processing system 32 to predict failures, to determine the impact of transient events, and to measure the effectiveness of service actions.

In one embodiment, based on the selected wavelet coefficient features, the data processing system 32 may model the relationship of a given value of the coefficients to a hazard function of failure. The baseline hazard function may relate coldhead life to the age of the coldhead 180 based on observed reliability of a population of similar coldheads 180. The baseline hazard function may then be modified multiplicatively by the addition of covariates X. For the coldhead 180, these covariates may represent the standard deviation of a detail coefficient and slope of the approximate coefficient, and may allow for directly relating the observed deterioration of the wavelet coefficient to the hazard function and, thus, to the estimated time to failure for the coldhead 180. The coefficients β for the covariates may be estimated using training data. Additionally, the model may allow for capturing the profile of the coldhead hazard function at different ages of the coldhead 180 by building the model based on sample data from similar coldheads of different ages. In one embodiment, the model may be described by:

$$h(t)=h_0(t)\exp(X\beta),$$

and may be used to calculate a predicted time to failure and the effect of an event on the life of the coldhead 180.

As discussed above, transient events (e.g., compressor reset) may be detected automatically by way of the wavelet analysis. Further, however, the impact of these detected events on the life of the coldhead 180 may be determined through analysis of changes in the observed hazard function. For instance, if $X_B$ and $X_A$ are the covariate measurements before and after occurrence of the event, the change in hazard function due to the event may be determined using the model described immediately above. Further, based on a predicted coldhead failure, a corrective service action can be performed to extend coldhead life (e.g., recharging compressor) or to replace the coldhead 180. The effectiveness of the service action in terms of recovery of the coldhead cycle can be used to determine the degree of renewal of the coldhead (which may generally correspond to a decrease in hazard rate based on $X_B$ and $X_A$). Based on estimated renewal for each service action, an optimal service action can be determined, as previously discussed above. It is noted that the optimal service action may depend on the age and operating state of the coldhead 180. For instance, recharge of the compressor may be the optimal service action for a relatively young coldhead 180, whereas replacement may be the optimal service action for an older coldhead 180.

Finally, after the recommended service action is performed, the actual renewal of the coldhead 180 may be compared to the predicted renewal of the coldhead 180 to determine effectiveness of the service action. Such a comparison may also be made upon replacement of a coldhead 180 with another coldhead 180. For instance, the hazard function of the replaced coldhead can be compared with an estimated hazard of a new coldhead (based on training data of coldhead replacements) to determine if the replacement was done effectively and if performance of the new coldhead 180 is within estimated limits. Accordingly, any faulty coldhead 180 or replacement issues can be identified based on this analysis.

Figure 10:
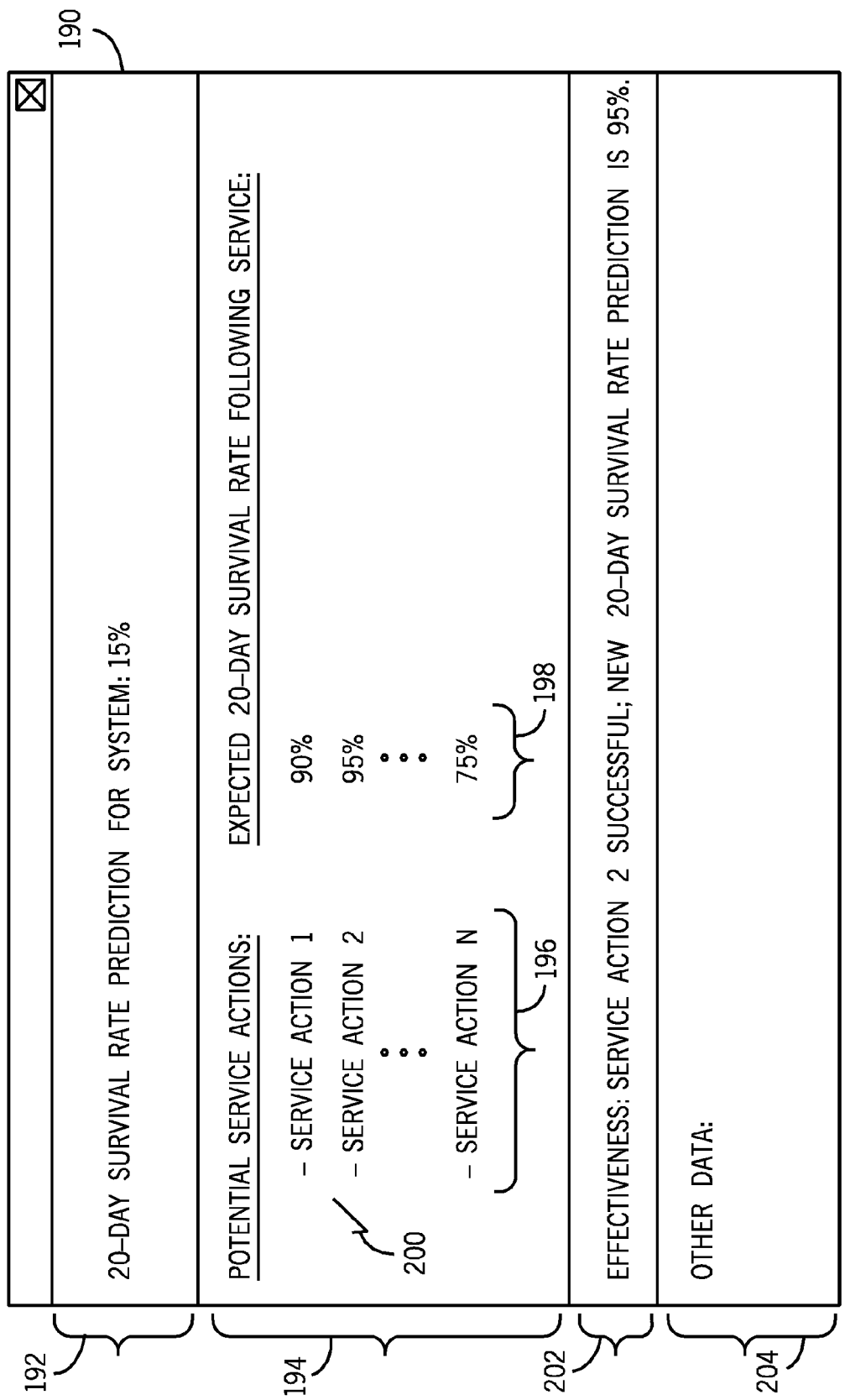
FIG. 10 is an example of a system report provided in a display window in accordance with one embodiment of the presently described subject matter.

As generally discussed above, various data, predictions, and results may be reported to a user in any suitable fashion, including, but not limited to, displaying or printing such items via the display 20 or the printer 22, respectively. In one example, such information may be displayed in a window 190 of the display 20, as depicted in FIG. 10 in accordance with one embodiment. In this presently illustrated embodiment, a survival rate prediction for a system, such as the scanner 168, is provided in a region 192 of the window 190. A region 194 of the window 190 may include a list of potential service actions 196 that may be performed on the system as well as a list of expected survival rates 198 of the system following such service actions. In one embodiment, in addition to indicating potential service actions 196, the data processing system 32 may determine a desired or optimal service action, as generally discussed above, and recommend a particular service action, as indicated by check mark 200. Once one or more of these potential service actions 196 have been performed on the system, the effectiveness of the one or more service actions 196 may be determined as discussed above and then displayed in a region 202. Additionally, other data, such as a suggested service time, technician notes, or the like, may be displayed in a region 204 of the window 190. It is noted that, while the information is presently depicted in a textual form in the window 190, information within the window 190 may also be provided in some other format, such as a graphical format. Still further, while certain types of information are presently illustrated in FIG. 10, it is noted that other embodiments may include different or additional information, including a predicted extension of operating life or other information described herein.

In some embodiments, technical effects of the present subject matter may include, among others, early detection of device or component deterioration and determination of an optimal service action for the device or component. Further, another technical effect may include determination of an estimated time to failure of the device or component, and the calculation of the effectiveness of a performed service action. Still further, an additional technical effect may include transient event detection and determination of the impact of such events on the life of a monitored device or component.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method comprising:
   obtaining operational data of a device of interest, the operational data including a feature of interest;
   applying a transform via a processor of a machine to extract the feature of interest from the operational data;
   comparing via the processor a characteristic of a transform coefficient associated with the extracted feature of interest to a threshold derived at least in part from a statistical analysis of a population of additional devices similar to the device of interest, wherein the threshold is derived by using a failure prediction model to calculate the threshold;
   calculating via the processor an operating state of the device of interest dependent at least in part on the comparison;
   using the failure prediction model to calculate the probability of device failure in a finite future time period;
   selecting a service action for the device based at least in part on the use of a reliability model, wherein selecting a service action includes calculating expected changes in the probability of device failure associated with execution of each of a plurality of potential service actions;
   receiving additional operational data from the device following execution of a service action;
   calculating the effectiveness of an executed service action via the additional operational data and the reliability model; and
   outputting a report indicative of the operating state of the device.

2. The method of claim 1, wherein the step of receiving the operational data of the device includes receiving a first set of operational data of the device collected before an event of interest and a second set of operational data of the device collected after the event of interest.

3. The method of claim 2, further comprising the steps of:
   applying a wavelet transform to each of the first and second sets of data to generate a first and second set of wavelet coefficients, respectively;
   detecting a change between the first and second sets of wavelet coefficients; and calculating a change in a life expectancy of the device dependent on the change between the first and second sets of wavelet coefficients.

4. The method of claim 1, further comprising the step of selecting the transform from a plurality of transforms to increase detection of a deterioration of the device, a transient event of the device, or a data trend in the operational data of the device.

5. The method of claim 1, wherein the step of applying the transform includes the step of applying a discrete wavelet transform.

6. The method of claim 1, wherein the step of comparing the characteristic of the transform coefficient includes the step of calculating a variance of the transform coefficient.

7. The method of claim 1, wherein the feature of interest includes a trend in a cyclic frequency in pressure data of a vessel.

8. The method of claim 1, wherein the report includes at least one of a forecast change in the probability of device failure based on execution of a potential service action, or an indication of the effectiveness of an executed service action.

9. The method of claim 1, wherein the report illustrates a comparison of survival rates of the device of interest before and after execution of a device service action, wherein the survival rates are determined through wavelet transform analysis.

10. A system comprising:
a medical device of interest including a device component;
monitoring circuitry configured to measure operational data of the device component; and
a data processing system configured to output a report based at least in part on an analysis of the operational data of the device component, wherein the analysis of the operational data includes applying a wavelet transform to separate at least one signal component in the operational data, and predicting at least one of a failure rate or a survival rate of the device component over a time period based at least in part on comparison of a coefficient characteristic of the wavelet transform to one or more threshold coefficient characteristics, wherein the one or more threshold coefficient characteristics are calculated at least in part from a statistical analysis of a population of additional medical devices similar to the medical device of interest, the data processing system further configured to calculate, based at least in part on the use of a reliability model, expected changes in the failure rate or in the survival rate associated with execution of each of a plurality of potential service actions for the medical device and select a service action for the medical device from the plurality of potential service actions, and configured to receive additional operational data of the device component following execution of the selected service action and calculate the effectiveness of the selected service action after execution via the additional operational data and the reliability model.

11. The system of claim 10, wherein the medical device of interest includes an imaging system.

12. The system of claim 11, wherein the imaging system includes a refrigeration system having the device component, and the operational data includes at least one of pressure data or temperature data related to the device component.

13. The system of claim 10, wherein the medical device includes the monitoring circuitry.

\* \* \* \* \*